United States Patent [19]
Trampe

[11] 3,987,546
[45] Oct. 26, 1976

[54] PROSTHETIC DENTURE AND METHOD OF MAKING SAME

[76] Inventor: Daniel E. Trampe, 10626 N. 44th Court, Phoenix, Ariz. 85028

[22] Filed: Apr. 2, 1975

[21] Appl. No.: 564,541

[52] U.S. Cl. .................................................. 32/2
[51] Int. Cl.² ........................................ A61C 13/00
[58] Field of Search ..................... 32/2, 8, DIG. 2

[56] References Cited
UNITED STATES PATENTS

| | | | |
|---|---|---|---|
| 2,985,961 | 5/1961 | Schwartz | 32/2 |
| 3,327,392 | 6/1967 | Grow | 32/2 |
| 3,667,123 | 6/1972 | Huey | 32/2 |
| 3,727,309 | 4/1973 | Huey | 32/2 |

*Primary Examiner*—Louis G. Mancene
*Assistant Examiner*—Jack Q. Lever
*Attorney, Agent, or Firm*—Drummond, Nelson & Ptak

[57] ABSTRACT

A prosthetic denture is disclosed. The denture includes an assembly of hard acrylic teeth bonded to a "semi-hard" acrylic base member. The base member is formulated from an acrylic polymer blend to yield preselected characteristics including hardness and thermal deformability so that fitting adjustments to conform to the wearer and to insure occlusive harmony can be accomplished with facility.

3 Claims, 6 Drawing Figures

PROSTHETIC DENTURE AND METHOD OF MAKING SAME

The present invention relates to a prosthetic denture and more particularly relates to a prosthetic denture having a uniform base structure having optimum characteristics for user comfort, convenience and ease of fitting.

Conventional prosthetic dentures have in the past been manufactured by setting individual teeth in a hard base structure formed from suitable plastics such as various hard acrylic resins. Conventional dentures are made by making an initial impression in a suitable soft material such as alginate. The initial impression is then used to form a custom tray. The tray, in turn, is then used to make a secondary impression from polysulfide rubber or other similar material. The final steps involve forming the denture in wax, investing, and lost wax techniques. The denture is then fitted to the wearer and suitably lined to conform to the wearer's edentulous ridge.

The initial impression and subsequent fittings all require several appointments with the dentist or technician and may require several weeks time. During the period of which the dentures are being custom made, the dental patient is often without the use of dentures or must have available a temporary or auxiliary set. Thus, conventional procedures impose a great inconvenience and possible embarrassment to the patient. In addition, conventional procedures involved in making and fitting dentures which require numerous patient visits for impression and fitting is not the most efficient utilization of the dentist's time.

In accordance with the partial recognition of these problems, the prior art contains a number of prosthetic dentures that may be more conveniently adapted to the particular mouth structure of the patient.

For example, it is known to form prosthetic denture devices using artificial teeth which are held in position by a rigid metal frame. A hard, rigid acrylic base material is bonded to the teeth and a semi-rigid resilient material is bonded to the tissue side surface of the base material. The semi-rigid base material is deformable above body temperature when it is heated sufficiently so that it can be conformed by a dentist to a proper dentally operative position in the patient's mouth.

However, improved prosthetic devices of the general type described above exhibit a number of disadvantageous characteristics. It has been generally thought that a metal frame or wire mesh or acrylic bar must be included in the base structure to support the teeth when the denture base comprises other than a hard acrylic. The inclusion of such a bar, wire or mesh adds to the cost and to the complexity of the resulting denture device. Further, the teeth remain set in the hard acrylic base material and are coupled to the reinforcing bar or mesh, be it metal or hard acrylic, so that substantial adjustments to adapt the denture to the physical configuration of the user's mouth are rendered difficult. Even the addition of an overlying layer of softer material does not entirely eliminate shock and destructive forces occurring during mastication. The hard base establishes the vertical height of the teeth over the edentulous ridge and limits fitting adjustment. If the teeth are inaccurately placed, even a small distance, destructive forces can work on the oral tissues during mastication. These forces can create inflammation and result in absorption of the bone of the edentulous ridge over a period of time.

In an attempt to avoid the shortcomings of the prior art dentures, the present invention provides a denture which can be produced in a range of preselected sizes and styles and which includes a base which is thermally deformable and can with ease and facility be conformed into a dentally operative condition in the wearer's mouth. Laborious and time consuming custom making and fitting techniques are completely obviated.

Briefly, the present invention provides an artificial denture comprised of the assembly of individual hard acrylic teeth. The hard acrylic teeth are set or bonded in a formulated acrylic material having optimized preselected mechanical characteristics including hardness and thermal deformation. The base material comprises a polymeric material which is specially adaptive to achieve the optimum characteristics for the dentures. The base material is firm at body temperature but at slight elevated temperatures can be modified to conform to the patient's mouth. Proper occlusion can be achieved by adjustment for centric, height, and width relationship of the denture teeth. Further, the charcteristics of the dental base material provide resiliency, as compared with prior art hard acrylic bases, which absorb the forces of shock due to mastication. Thus, the present invention contemplates a denture having rigid teeth set in a soft or semi-hard base which is capable of being deformed at the time of fitting to a dentally correct configuration. Over prolonged use, the denture of the present invention will minimize irritating forces imparted to the mouth of the user during use. It is noted that even though the denture of the present invention can be conventionally fitted, it is intended for use only by qualified dentists in accordance with American Dental Association practices.

Further objects and advantages will become apparent from the following specification, claims and accompanying drawings in which:

Figure 1:
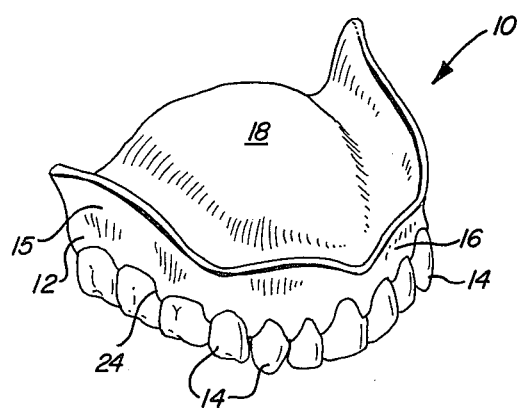
FIG. 1 is a perspective view of the maxilliary denture formed of a resilient base material in accordance with the present invention.
Figure 2:
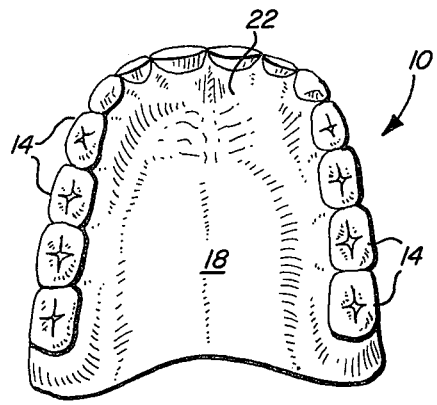
FIG. 2 is a plan view of the tooth sides of a maxilliary denture showing the teeth set in the soft resilient denture material.

Referring now to the drawings, FIG. 1 illustrates as assembly of artificial teeth generally designated by the numeral 10. The set 10 is a maxilliary or upper denture and it will be appreciated that the following description is equally applicable to the lower mandibular denture. However, for clarity and purposes of illustration, the present invention will be described with reference to the maxilliary prosthetic denture device. The denture assembly 10 comprises a base member 12 which is molded or cast form polymeric resins having preselected properties which result in a base of specific properties as will be described hereafter.

Preferably the base member is formed of acrylic polymers. The term "acrylic" is broadly used to include the group of thermoplastic resins synthetically produced by polymerizing the esters of acrylic acid. Generally, methacrylate is a primary constitute of such material. However, materials may also contain polystyrene, polyvinyl chloride, polyvinly acetate and other polymers and monomers. These types of materials are well known in the art and need not be described in detail hereafter.

Figure 3:
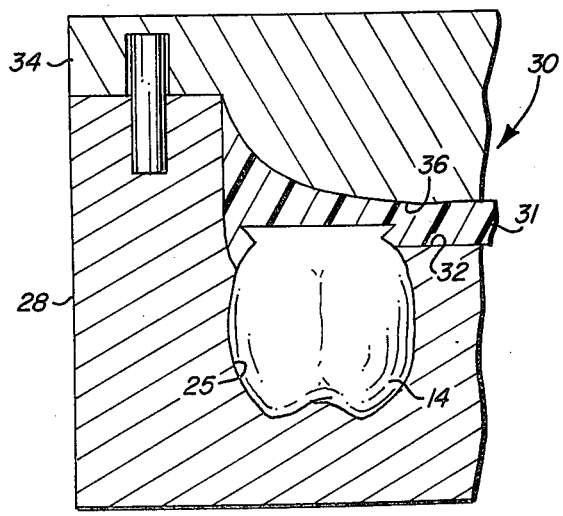
FIG. 3 is a cross-sectional view of the prosthetic denture in accordance with the present invention.
Figure 4:
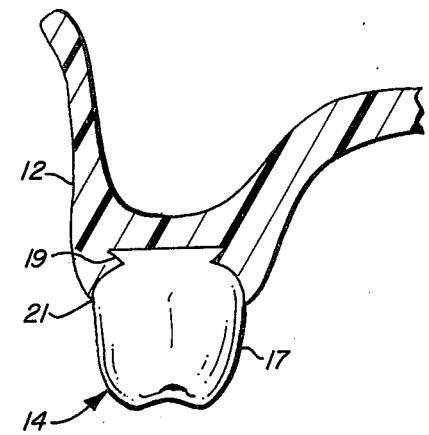
FIG. 4 is a partial cross-sectional view of a mold showing an artificial denture of the invention therein and as produced in accordance with the method of the present invention.

Denture base 12 supports a set of artificial teeth 14 which duplicate natural human teeth extending from the posterior molars to the anterior incisors. Teeth 14 are preferably formed of a hard acrylic material such as specified by the American Dental Association Specification No. 15. The preferred tooth construction is best seen in FIG. 3. Each tooth 14 has a crown portion 17 and a neck portion 23. The neck portion 23 is embedded in the dental base 12 below the gingival line 21. Neck 23 is preferably undercut at 19 so the base material fills the undercut region 19 to form a stronger bond.

The dental base 12 includes buccal flanges 15 projecting at either side of the base member 12. The forward portion of the buccal flanges converge in a U-shape forming labial flange 16. An arched or convex palate plate 18 extends laterally between the opposite buccal flanges 15. An edentulous ridge 20 is formed in the palate plate 18 and conforms generally to the edentulous. Palate plate 18 extends rearwardly to a location corresponding to the fovia palletine. The tooth side of the palate plate 18 is formed having ridges 22 similar to the rugae occurring in the human mouth. Appropriate festooning extends along the gingival line 21 in the inter-proximal tooth area.

Base 12 is a semi-hard acrylic blend resulting in a tooth support having several highly desirable characteristics. The base has the properties necessary for use as a denture base and is compatible with the conditions existing within the human mouth. These criteria, as established by the American Dental Association, include the structural and mechanical integrity to secure the teeth in place and sufficient rigidity to maintain the denture in position while chewing. In addition, the base material must be odorless, tasteless, easily cleaned, abrasion resistant, stain resistant, have low absorption characteristics and be chemically stable. Another important characteristic of the base 12 of the present invention is its hardness which provides shock absorbing characteristics to dampen forces transmitted to the bone structure of the mouth. The material of the denture base is pliable and is thermally deformable to permit the dentist to conform the denture to the specific physical characteristics of the wearer's mouth.

Accordingly, the present invention will be better understood from the following description of the method of making a denture. In accordance with the method invention, the artificial teeth 14 are arranged in cavities 25 of a lower mold block 28 of mold set 30. Mold block 28 is preferably a silicone rubber or a suitable urethane. Teeth 14 are arranged conventionally having molar, cuspids, bi-cuspids, incisors, etc. The spacing and arrangement of teeth may be varied somewhat within rather narrow limits. It has been found that physical differences in the mouths of various humans are relatively small. For example, the curve of spee generally approximates four and one-half inches and the lateral spacing between the rear molars closely approximates 2 inches. Therefore, mold set 30 can be established in several preseleted sizes to cover the range of physical variances commonly found in the human mouth. In this way a number of preselected standard size dentures can be made. Accordingly, a dentist can stock these standard sizes and select the size that most nearly corresponds to the patient to minimize fitting adjustments.

After the lower teeth are appropriately placed in cavities or recesses 25 and lower mold block 28, the polymeric base material 31 will be prepared. The resulting denture base material is "semi-hard," having a durometer or hardness, Type A-2, in the range of from 90 to 100. The durometer test description, specification can be found in ASTM D 2240. In addition, the resulting cured base should have a softening range in warm water of from approximately 120° to 140° F.

It will be obvious to those skilled in the art that many different polymeric materials can be employed which have the above-described cured properties and it is not critical in the practice of the invention to use any specific polymer or polymer blend so long as the cured properties exhibit the proper hardness and softening temperature range and so long as the polymeric material is compatible with human mouth tissue over extended period of time.

Purely as a matter of convenience, in the presently preferred embodiment of the invention, I employ a blend of two commerically available acrylic resins—a so-called "hard" resin commercially available under the trade name "TruLiner" from the Harry J. Bosworth Company of Chicago, Ill., and a somewhat softer material commercially available under the trade name "Tru Soft," also available from the same company. The components of these resins are available to kit form which includes a powder material and a liquid component. Under normal circumstances where each material is to be used separately, the powder and liquid components are thoroughly mechanically mixed, the resulting rubbery mass is then shaped in a mold, and then the shaped resin is cured in hot water at approximately 140° F.

In order to prepare a base material having the proper cured characteristics, I dry-mix equal weights of the powdery components and then add a sufficient amount of the liquid component and continue mixing until the polymer reaches a doughy state. Then the teeth 14 are disposed in the lower mold block 28, the doughy base compound 31 is placed in the cavity 32 of the mold block 28. The doughy plastic material 31 is carefully pressed in place to fill all voids and to completely fill the mold contour and to flow into the undercut region 19 of each tooth. Once mold cavity 28 is filled with soft plastic material, upper mold member 34 is pressed into mating engagement with lower mold portion 28. The upper mold section 34 preferably may be an appropriate dental stone and has a surface 36 which conforms to the tissue side of the human mouth. Surface 36 imparts proper shape to the palate plate and forms the edentulous ridge 20 in the soft acrylic plastic material. The material is then allowed to cure for a predetermined time. As described above, the curing preferably occurs at a slightly elevated temperature.

Once the plastic material is hardened, the upper mold block 34 can be removed and cooled or chilled for handling. The coating of a release agent on the surface 36 of the mold facilitates separation of the mold block 34 from the completed denture 10. The denture can then be removed from the lower mold 28. Preferably, the mold block portion 28 and 34 are provided with inter-engaging shoulders or alignment pins to insure that the mold blocks are in proper registry.

Figure 5:
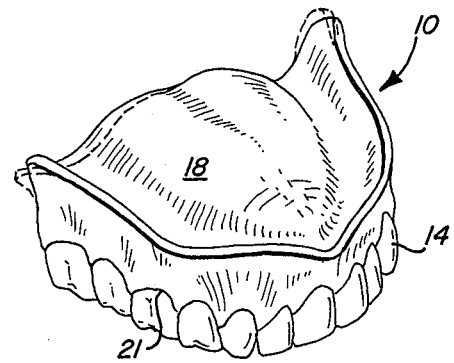
FIG. 5 is a perspective view of the maxilliary denture illustrating how the denture of the present invention may be deformed to the correct dentally operative position for a specific patient.
Figure 6:
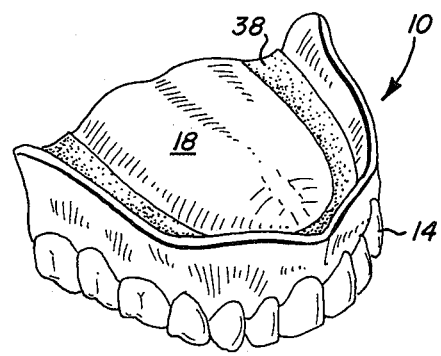
FIG. 6 is a perspective view of the maxilliary denture illustrating the final step in custom fitting the denture of the present invention.

The denture is now substantially completed as shown in FIG. 5. Any polishing or deburring to remove rough surfaces may be done at this time. As pointed out above, the completed denture will be made available in a preselected number of standard sizes to accommodate the various physical differences in the human mouth. Slight variations may also occur in the size and coloration of the teeth to best suit the cosmetic requirements of the user. The fitting of a complete set of dentures can be accomplished in a single dental appointment. The dentist will select one of the standard denture sets for the patient's use. The selected denture being matched with the patient's mouth and personal preference. The denture is placed in the patient's mouth and adjustments are noted. The denture is then removed and is warmed, preferably in a liquid medium, to approximately 120° to 140° F. This slight warming will soften the acrylic base material sufficiently to render it pliable and deformable. The dentist can then deform the denture base to intimately match the user's mouth. FIG. 5 illustrates typical adjustments that would be made at the time of fitting. The denture is then re-inserted in the patients's mouth to check proper fitting. If additional adjustments are required, heating and deforming can be repeated until an exact fit is accomplished.

Subsequent to fitting the denture, a conventional denture liner 38 can be applied to the tissue side of the palate plate 18 of the denture. A number of conventional liners are available such as those sold by the Harry J. Bosworth Company under the trademarks Tru Liner and Per-Fit Resilient Liner.

The fitting of the teeth is now substantially complete. The teeth can now be checked for occulsive alignment and harmony. Both vertical and centric adjustment can be made if necessary. The upper and lower prosthetic dentures are placed in position and the teeth guided into occlusion to see if proper alignment exists. Inaccurate placement or alignment of the fixed teeth will allow destructive forces during mastication to work on the soft oral tissues of the edentulous ridge and on the supporting bone structure. Over a period of time, these forces will create inflammation of tissue and bone loss. Prior art dental prosthetic devices which have been made entirely of hard acrylic or include only a layer or lamina of soft material only permit limited adjustment of tooth position. Generally, prior art prosthetic devices utilize at least a hard denture base which cannot be changed or must be heated to substantially elevated temperature to allow any realignment of the teeth. Further, many of these devices include metal wires or mesh which also must be bent or shaped to accommodate tooth adjustment. With the prosthetic device of the present invention, adjustment of the position of the teeth relative to the base and conforming to the base to conform the patient's mouth and easilly be accomplished with facility and ease at the time of setting. It will be obvious that the present denture can also be utilized as a temporary denture in case of emergency due to the ease with which it can be fitted.

In addition to providing substantial advantages at the time of fitting, the unitary base structure provides substantial advantages over prolonged use. The individual teeth are permitted limited movement relative to one another during mastication which minimizes the tendency of the base to tip or become dislodged from the edentulous ridges of the user. Further, the soft base material acts as a shock absorber to dampen and absorb forces imposed during mastication reducing the possibility of the patient's tissue and bone structure being irritated. The patient can accept a denture of the type described herein with substantially a less agonizing learning process. Muscle control and physiological adjustment are quickly made. Sore spots and tender spots are reduced.

Thus, the present invention provides a dental prosthetic device which provides substantial advantages over the prior art. It will be obvious to those skilled in the art to make various changes, alterations and modifications to the embodiments herein described. To the extent that these alterations, changes and modifications do not depart from the spirit and scope of the appended claims, they are intended to be encompassed therein.

I claim:
1. The method of manufacturing and fitting a prosthetic denture device comprising:
   a. manufacturing the denture device including the steps of:
      i. placing a plurality of individual artificial acrylic teeth in a mold,
      ii. placing a polymeric material in said mold, said polymeric material when cured having durometer hardness of from 90 to 100 and thermal deformabilty above 120° F,
      iii. forming said polymeric material into a denture base having said teeth embedded therein and conforming to the shape of the human mouth,
      iv. curing said material at a temperature of from about 140° to 200° F, and
      v. cooling said denture and removing from said mold;
   b. fitting said denture including the steps of:
      i. selecting a denture in accordance with the patient's requirements,
      ii. placing said denture in the mouth of the patient to determine the necessary fitting adjustments,
      iii. removing said denture from the patient's mouth and heating the denture base to a temperature of from about 120° to 140° F,
      iv. manually deforming said denture base to conform to the patient's mouth, and
      v. lining the denture base in the area of the edentulous ridge.
2. A prosthetic denture device comprising:
   a. at least one artificial tooth having a crown portion and a neck portion; and
   b. a unitary denture base material encasing the neck portion of said tooth and conforming to the shape of a portion of the human mouth, said base being a polymeric material which is compatible with human mouth tissue for extended periods and has the following mechanical charcteristics when cured:
      i. durometer hardness of from about 90 to 100, and
      ii. thermal deformability when heated to about 120° to 140° F.
3. The denture device of claim 2 wherein said tooth is undercut in the neck region.

* * * * *